United States Patent [19]
Dubief et al.

[11] Patent Number: 5,324,507
[45] Date of Patent: Jun. 28, 1994

[54] COMPOSITION FOR WASHING BASED ON HYDROCARBON OIL AND FATTY ALCOHOLS CONTAINING ETHER AND/OR THIOETHER OR SULPHOXIDE GROUPS

[75] Inventors: Claude Dubief, Le Chesnay; Daniele Cauwet, Paris, both of France

[73] Assignee: L'Oreal, Paris, France

[21] Appl. No.: 828,666

[22] Filed: Feb. 6, 1992

[30] Foreign Application Priority Data

Feb. 6, 1991 [FR] France .................. 91 01330

[51] Int. Cl.$^5$ .................................. A61K 7/06
[52] U.S. Cl. ........................ 424/70; 424/401; 514/939; 514/942; 252/DIG. 4; 252/DIG. 5
[58] Field of Search .................. 424/401, 70; 252/DIG. 4, DIG. 5; 514/942, 939

[56] References Cited

U.S. PATENT DOCUMENTS 3,818,105  6/1974  Coopersmith et al. .............. 424/70
3,998,948  12/1976  Vanlerberghe et al. ............ 514/942

Primary Examiner—Thurman K. Page
Assistant Examiner—Jyothsna Venkat
Attorney, Agent, or Firm—Jacobson, Price, Holman & Stern

[57] ABSTRACT

The invention relates to a composition for washing keratinous materials, in particular the hair and/or the skin, comprising, in an aqueous medium, at least one hydrocarbon oil, at least one surface-active agent possessing detergent properties and at least one alcohol having 17 to 44 carbon atoms and containing one or two ether and/or thioether or sulphoxide groups, of the formula (I):

$$R_1-X-[C_2H_3(OH)]-CH_2-Y-R_2 \qquad (i)$$

in which
  $R_1$ and $R_2$, which are identical or different, denote linear $C_{12}$ to $C_{20}$ alkyl groups;
  X denotes an oxygen atom, a sulphur atom or a sulphoxide group;
  Y denotes an oxygen atom, a sulphur atom, a sulphoxide group or a methylene group;
  in the case where Y denotes a methylene group, the sum of then umber of carbon atoms in $R_1$ to $R_2$ ranges from 24 to 40, and when Y does not denote a methylene group, the sum of the carbon atoms in $R_1$ and $R_2$ ranges from 24 to 40 inclusive; when X or Y denotes sulphoxide, Y or X does not denote sulphur.

28 Claims, No Drawings

COMPOSITION FOR WASHING BASED ON HYDROCARBON OIL AND FATTY ALCOHOLS CONTAINING ETHER AND/OR THIOETHER OR SULPHOXIDE GROUPS

The invention relates to compositions for washing and conditioning keratinous materials, in particular the hair and/or the skin, based on oil, detergent surface-active agents and a fatty alcohol containing an ether and/or thioether or sulphoxide group, as well as to the methods of washing using these compositions.

Compositions for washing keratinous materials, in particular shampoos, are well known in the state of the art. It has already been proposed in the past to use oils in such compositions, in particular with the aim of simultaneously treating dry hair during washing in order to confer on it properties of softness and sheen.

The oils which are capable of being used in compositions for washing and conditioning keratinous materials are, however, generally insoluble, so that it is sought to maintain the oils as a fine and uniform dispersion in the medium without, however, causing a drop in the viscosity and the detergent and foaming properties of the compositions.

The oils must also be carried onto the treated keratinous materials in order to confer on them softness, sheen and disentangling properties, following the application.

The Applicant has discovered, and this constitutes the subject of the invention, that by using in aqueous compositions for washing based on insoluble hydrocarbon oils and detergent surface-active agents, at least one alcohol having 27 to 44 carbon atoms and comprising one or two ether and/or thioether or sulphoxide group(s), it was possible to prepare compositions containing an oil, possessing a very good homogeneity and an improved stability, as well as a satisfactory viscosity for application to keratinous materials, in particular to the hair or to the skin.

The compositions thus prepared also possess good detergent and foaming properties and confer great softness on the keratinous materials, in particular the hair and/or the skin.

These compositions possess hair conditioning properties in addition to their washing properties, when they are applied to hair. Conditioning refers to the properties of sheen, easy disentangling and softness to tough. Moreover, it is observed that the hair is not made lank after several applications.

The subject of the invention is therefore novel aqueous compositions for washing based on hydrocarbon oils, detergent surface-active agents and ether and/or thioether or sulphoxide alcohols, in the form of a suspension.

Another subject of the invention consists of the method of washing using such compositions.

The subject of the invention is also the use of ether and/or thioether or sulphoxide alcohols defined below as agents for suspending oil in an aqueous medium containing detergent surface-active agents.

Other subjects of the invention will emerge from reading the following description and examples.

The compositions for washing keratinous materials, in particular the hair and the skin, conforming to the invention, comprise, in an aqueous medium, at least one hydrocarbon oil, one surface-active agent possessing detergent properties and at least one alcohol having 27 to 44 carbon atoms and comprising one or two ether and/or thioether or sulphoxide group(s) of the formula (I):

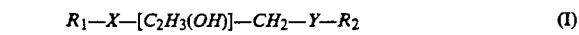

$$R_1-X-[C_2H_3(OH)]-CH_2-Y-R_2 \quad (I)$$

in which
- $R_1$ and $R_2$ denote, independently of each other, linear $C_{12}$ to $C_{20}$ alkyl groups;
- X denotes an oxygen atom, a sulphur atom or a sulphoxide group;
- Y denotes an oxygen or sulphur atom, or a sulphoxide or methylene group;
- in the case where Y denotes a methylene group, the sum of the number of carbon atoms present in the $R_1$ and $R_2$ groups has a value ranging from 24 to 40 and preferably from 26 to 36 inclusive;
- when Y does not denote a methylene group, the sum of the $R_1$ and $R_2$ carbon atoms has a value ranging from 24 to 40 inclusive and preferably from 28 to 36 inclusive;
- when X or Y denotes sulphoxide, Y or X does not denote sulphur.

The compounds preferably used in conformity with the invention are those in which X denotes oxygen, Y denotes methylene, and $R_1$ and $R_2$ radicals having 12 to 18 carbon atoms.

The compounds of formula (I) are obtained by reacting an active hydrogen-containing compound of formula (II):

$$R_1XH \quad (II)$$

with a compound containing a terminal oxirane group and of the formula (III):

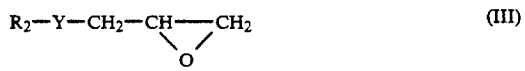

$$R_2-Y-CH_2-CH\underset{O}{\overset{}{\diagdown\!\!\diagup}}CH_2 \quad (III)$$

When X denotes oxygen, these reactions are carried out preferably in the presence of a molar excess of the compound of formula (II) relative to the compound of formula (III), it being possible for this excess to be as high as five times the stoichiometric amount, in the presence of an acidic catalyst such as for example boron trifluoride, $SnCl_4$ or $ZnCl_2$ or in the presence of an alkali metal catalyst such as sodium, potassium, sodium or potassium methylate, ethylate or tert-butylate.

Using an acidic catalyst, the reaction temperature is between 40° C. and 100° C.; using an alkali metal catalyst, it is preferably between 80° C. and 180° C.

When one of the groups X or Y denotes a sulphur atom, the reaction is preferably carried out using an alkali metal catalyst and with stoichiometric proportions of the compounds of formulae (II) and (III).

The proportion of catalyst used is generally 0.1 to 3% by weight relative to the weight of the reaction mass.

Depending on the side on which the epoxide of formula (III) is opened, there may be obtained the following isomeric of formulae (Ia) and (Ib):

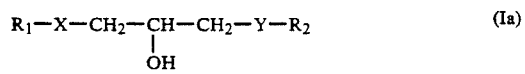

$$R_1-X-CH_2-\underset{\underset{OH}{|}}{CH}-CH_2-Y-R_2 \quad (Ia)$$

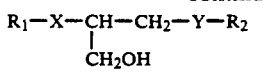

The compounds of formula (I) may be purified, after removal under reduced pressure of the residual active hydrogen-containing compound of formula (II), by molecular distillation, preferably under about $10^{-3}$ mm of mercury (0.13 Pascal).

When the starting compound of formula (II) is an alcohol, it is also possible to use, within the framework of the invention, the reaction product after simple partial or total removal of the excess alcohol of formula (II), or even the crude reaction product, that is to say while retaining all the excess fatty alcohol of formula (II). Indeed, the fatty alcohols of formula (II), used within the framework of the preparation of the compounds of formula (I) used in conformity with the invention, are not prejudicial to the expected properties of the compounds of formula (I) and they may contribute to stabilising and opacifying the detergent compositions.

The compounds of formula (I) in which at least one of the groups X or Y denotes a sulphur atom may be oxidised, using conventional methods, to sulphoxides which are of the formula (IV):

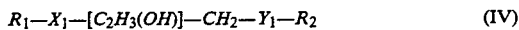

in which $R_1$ and $R_2$ have the same meanings as in formula (I); $X_1$ denotes an oxygen atom or a sulphoxide group; $Y_1$ denotes an oxygen atom, a methylene or sulphoxide group, at least one of the symbols $X_1$ or $Y_1$ represents a sulphoxide group.

"Hydrocarbon oil" refers to a compound which is liquid at room temperature, is insoluble in water and is of hydrophobic character.

The hydrocarbon oils used in conformity with the invention are synthetic oils, mineral, vegetable or animal oils, unsaturated fatty alcohols, and esters of fatty acids and lower $C_2$-$C_4$ mono- or polyalcohols.

Among the synthetic oils may be mentioned the isoparaffins of the formula:

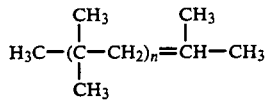

in which n ranges form 2 to 16.

These isoparaffins may be used alone or mixed with other isoparaffins of higher molecular weight and which are of the formula (VI):

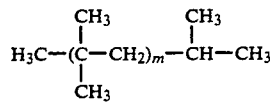

where m is not less than 18 and is preferably between 18 and 40.

Among the compounds of formula (V), there may be mentioned more particularly the products sold under the name PERMETHYL 99A, 101A, 102A or 104A, corresponding to the n values 2, 3, 4 and 16 respectively, sold by PRESPERSE INC. or the products sold under the name ARLAMOL HD by ICI, corresponding to the formula (V), in which n is equal to 3.

Among the compounds of formula (VI), there may be mentioned the product sold under the name PERMETHYL 106A, in which m is equal to 38.

Another category of synthetic oils is composed of $C_6$-$C_{12}$ fatty acid triglycerides.

Liquid paraffin may be mentioned among the mineral oils.

The animal oils are chosen from naturally or chemically saturated oils such as squalene, but whale, seal, menhaden, halibut liver, cod liver, tuna fish, tallow, beef, caballine, mutton, vison or otter oil may also be mentioned.

Among the vegetable oils, there may be mentioned almond, peanut, wheat-germ, linseed, apricot stone, nut, palm, pistachio, sesame, poppy seed, pine, castor, soya bean, avocado, safflower, coconut, hazelnut, olive, grape seed, sunflower, colza, cade, maize-germ, peach stone, coffee, jojoba oils and the like. Naturally or chemically saturated oils are preferred.

The aforementioned oils may be used mixed with the compositions conforming to the invention.

The surface-active agents used in the compositions for washing conforming to the invention are chosen from anionic, amphoteric, zwitterionic or non-ionic surface-active agents or their mixtures, having detergent properties.

Among the anionic surface-active agents, there may be mentioned the alkali metal salts, the ammonium salts, the amine salts, the aminoalcohol salts, or the magnesium salts of the following compounds: alkyl sulphates, alkyl ether sulphates, alkylamidoether sulphates, alkylarlyl polyether sulphates, monoglyceride sulphates; alkylsulphonates, alkylamide sulphonates, alkylarylsulphonates, olefinsulphonates, paraffin sulphonates; alkyl sulphosuccinates, alkyl ether sulphosuccinates, alkylamide sulphosuccinats; alkyl sulphosuccinamates; alkyl sulphoacetates; alkyl phosphates, alkyl ether phosphates; acyl sarcosinates, acyl isethionates and N-acyltaurates.

The alkyl or acyl radical in these various compounds generally consists of a carbon chain containing 12 to 20 carbon atoms.

Among the anionic surface-active agents, the fatty acid salts such as the salts of oleic, ricinoleic, palmitic and stearic acids; copra oil or hydrogenated copra oil acids and acyl lactylates whose acyl radical contains 8 to 20 carbon atoms, may also be mentioned.

Surface-active agents considered as weakly anionic such as polyoxyalkylenated carboxylic ether acids may also be used.

The non-ionic surface-active agents are more particularly chosen from polyethoxylated, polypropoxylated or polyglycerolated alcohols or alkylphenols or fatty acids, with a fatty chain containing 8 to 18 carbon atoms, the number of ethylene oxide or propylene oxide groups being between 2 and 50 and the number of glycerol groups being between 2 and 30.

The copolymers of ethylene and propylene oxides; the condensates of ethylene and propylene oxides with fatty alcohols; polyethoxylated fatty amides preferably having 2 to 30 moles of ethylene oxide; polyglycerolated fatty amides preferably containing 1 to 5 glycerol groups and in particular 1.5 to 4; polyethoxylated fatty amines preferably having 2 to 30 moles of ethylene oxide; oxyethylenated sorbitan fatty acid esters with 2 to 30 moles of ehtylene oxide; sucrose fatty acid esters, polyethylene glycol fatty acid esters, ($C_8$–$C_{18}$ alkyl)polyglucosides, amine oxides such as alkylamine or N-acylamidopropylmorpholine oxides, may also be mentioned.

The preferred amphoteric or zwitterionic surface-active agents are the aliphatic secondary or tertiary amine derivatives in which the aliphatic radical is a linear or branched chain containing 8 to 18 carbon atoms and which contains at least one anionic water-solubilising carboxylate, sulphonate, sulphate, phosphate or phosphonate group; ($C_8$–$C_{20}$ alkyl)betaines, sulphobetaines, ($C_8$–$C_{20}$ alkyl)amido ($C_1$–$C_6$ alkyl) betaines or ($C_8$–$C_{20}$ alkyl)amido($C_1$–$C_6$ alkyl)sulphobetaines.

Among the amine derivatives, there may be mentioned the products sold under the name MIRANOL, such as described in U.S. Pat. Nos. 2,528,378 and 2,781,354 and classified in the CTFA dictionary, 3rd Edition, 1982, under the name Amphocarboxyglycinates and Amphocarboxypropionates.

The hydrocarbon oils are used in the compositions conforming to the invention in proportions preferably of between 0.05 and 20% and preferably between 0.1 and 10% by weight relative to the total weight of the composition.

The alcohols containing ether and/or thioether or sulphoxide group(s) of the formula (I) or of the formula (IV) which are used in conformity with the invention are present in proportions sufficient to ensure the suspension of the hydrocarbon oils in the compositions and preferably in proportions of between 0.1 and 20% by weight relative to the total weight of the composition and in particular between 0.5 and 10%.

The surface-active agents are used in the compositions conforming to the invention in proportions sufficient to confer a detergent character on the composition and are preferably between 5 and 50% by weight relative to the total weight of the composition and in particular between 8 and 35%.

The compositions according to the invention possess a pH generally between 2 and 9 and more particularly between 3 and 8.

The aqueous medium of the compositions is composed either of water or of a mixture of water and a solvent or solvents chosen from lower alcohols, alkylene glycols and glycol ethers; the water being present in proportions above 20% and preferably above 45%.

The compositions according to the invention may also contain viscosity regulating agents such as electrolytes such as sodium chloride or sodium xylenesulphonate, hydrotropic agents, thickeners such as cellulose derivatives such as for example carboxymethyl-cellulose, hydroxypropylcellulose, hydroxyethyl-cellulose, guar gum, hydroxypropylated guar gums, scleroglucans and xanthan gum.

These viscosity regulating agents are used in proportions ranging up to 15% by weight relative to the total weight of the compositions and preferably less than 6%.

The compositions conforming to the invention may optionally contain, in addition, other agents, provided that they do not alter the stability of the compositions, such as cationic surface-active agents, polymers or quaternised or non-quaternised proteins, silicone oils, waxes, gums or resins.

The polymers, cationic surface-active agents and quaternised or non-quaternised proteins, and the silicones are used in the cosmetic or dermatological compositions according to the invention in proportions of between 0.05 and 6% and preferably between 0.1 and 3% relative to the total weight of the composition.

The compositions according to the invention may also contain various adjuvants normally used in cosmetics, such as perfumes, preservatives, sequestrants, foam stabilisers, propelling agents, colorants, acidifying or alkalinising agents or other adjuvants depending on the use envisaged.

The dermatological compositions in addition contain a substance which is active in the treatment of dermatological disorders.

The method for washing and/or conditioning the hair or the skin consist in applying to them a composition as defined above, this application being followed by rinsing.

The compositions conforming to the invention may also be used as shower gels for washing the hair and the skin, in which case they are applied to wet skin and hair and are rinsed after application.

The following examples are intended to illustrate the invention without, however, being of a restrictive nature.

EXAMPLE 1

The following composition is prepared:

| | |
|---|---|
| Sodium lauryl ether sulphate | 10.0 g |
| Ammonium lauryl sulphate | 8.0 g AS |
| Sodium chloride | 3.25 g |
| Compound of formula (I), in which: | 2.5 g |
| $R_1 = C_{16}H_{33}$, $R_2 = C_{14}H_{29}$ | |
| $X = O$, $Y = CH_2$ | |
| prepared by reacting 3 moles of alcohol with 1 mole of epoxide, used in the crude state | |
| Copra acid monoisopropanolamide | 2.0 g |
| Isooctahexacontane (compound of formula (I) in which n = 16) | 0.5 g |
| Isohexadecane (compound of formula (I) in which n = 3) | 0.8 g |
| Preservatives, perfumes | |
| Water qs | 100.0 g |
| pH adjusted to 6.3 with sodium hydroxide | |

This composition is used as shampoo for washing the hair.

EXAMPLE 2

The following composition is prepared:

| | |
|---|---|
| Sodium lauryl ether sulphate | 1.5 g AS |
| Lauryl betaine sold by HENKEL under the commercial name DEHYTON AB 30 in an aqueous solution containing 32% of AS | |
| Isohexadecane (Permethyl 101A from PRESPERSE INC.) (Compound of formula (I) in which n = 3) | 2.5 g AS |
| Compound of formula (I), in which: | 2.5 g |
| $R_1 = C_{16}H_{33}$, $R_2 = C_{14}H_{29}$ | |
| $X = O$, $Y = CH_2$ | |
| prepared by reacting 3 moles of alcohol with 1 mole of epoxide used in the crude state | |
| Oxyethylenated ($C_{13}$–$C_{15}$ alkyl)ether-carboxylic acid monoethanolamide containing 2 moles of ethylene oxide, sold under the name AMINOL A 15 by CHEM Y | 2.0 g |
| Preservatives, perfumes, colorants | |
| Water qs | 100.0 g |
| pH adjusted to 6.5 with sodium | |

| | |
|---|---|
| hydroxide | |

This composition is used as shampoo for washing the hair.

EXAMPLE 3

The following composition is prepared:

| | |
|---|---|
| Ammonium lauryl sulphate | 8.0 g |
| Sodium lauryl sarcosinate | 5.0 g |
| Compound of formula (I), in which: | 3.0 g |
| $R_1 = C_{12}H_{25}$ | |
| $X = O, Y = CH_2$ | |
| $R_2 = C_{12}H_{25}/C_{14}H_{29}$ (50/50 in mole) | |
| prepared by reacting 3 moles of | |
| alcohol with 1 mole of epoxide and | |
| then distilling the excess alcohol | |
| Heptamethylnonane (compound of | 1.0 g |
| formula (I) in which n = 3) | |
| (ARLAMOL HD from ICI) | |
| HCl qs pH 6.5 | |
| Preservatives, perfumes qs | |
| Water qs | 100.0 g |

This composition is used as shampoo for washing the hair.

EXAMPLE 4

The following shower gel composition is prepared:

| | |
|---|---|
| ($C_8$–$C_{10}$ alkyl)polyglucoside in aqueous solution containing 60% of AS, sold under the name TRITON CG 110 by SEPPIC | 45.0 g AS |
| Compound of formula (I), in which: | 0.5 g |
| $R_1 = C_{16}H_{33}$ | |
| $R_2 = C_{14}H_{29}$ | |
| $X = O, Y = CH_2$ | |
| prepared by reacting 3 moles of alcohol per mole of epoxide used in the crude state | |
| Perhydrosqualene sold under the name COSBIOL by LASERSON SABETAY | 0.1 g |
| Cetyltrimethylammonium chloride in aqueous solution containing 25% of AS, sold under the name DEHYQUART A by HENKEL | 1.0 g AS |
| Perfume, preservative, colorant qs | |
| Water qs | 100.0 g |
| pH adjusted to 6 with triethanolamine | |

EXAMPLE 5

The following shower gel composition is prepared:

| | |
|---|---|
| ($C_{10}$~$C_{12}$–$C_{14}$ alkyl)polyglucoside (mean number of glucoside unit = 1.4) in aqueous solution containing 55% of AS, sold under the name ORAMIX WS 10 by SEPPIC | 45.0 g AS |
| Compound of formula (I), in which: | 0.5 g |
| $R_1 = C_{16}H_{33}$ | |
| $R_2 = C_{14}H_{29}$ | |
| $X = O, Y = CH_2$ | |
| prepared by reacting 3 moles of alcohol per mole of epoxide used in the crude state | |
| Colza oil (oleic, linoleic, linolenic acid triglycerides 50/20/10) | 10.0 g |
| Cetyltrimethylammonium chloride in aqueous solution containing 25% of AS, sold under the name DEHYQUART A by HENKEL | 1.0 g AS |
| Colorant, preservative, perfume qs | |
| Water qs | 100.0 g |
| pH adjusted to 6 with triethanolamine | |

The following shampoo is prepared:

| | |
|---|---|
| Sodium ($C_{12}$–$C_{14}$) alkyl ether sulphate containing 2 moles of ethylene oxide sold under the name EMPICOL ESB/3 FL by HENKEL in aqueous solution containing 28% of AS | 17.0 g AS |
| Sodium cocamidoethyl-N-(hydroxyethyl)-N-(carboxymethyl)glycinate | 8.0 g |
| 3'-Hexadecyloxy-2'-hydroxy-1-propyloxyhexadecane, compound of formula (I), in which: | 10.0 g |
| $R_1 = R_2 = C_{16}H_{33}$ | |
| $X = Y$ = oxygen | |
| Colza oil | 0.1 g |
| Colorant, preservative, perfume qs | |
| Water qs | 100.0 g |

What is claimed is:

1. Composition for washing the hair and/or the skin comprising, in an aqueous medium, between 0.05 and 20% by weight relative to the total weight of the composition of at least one hydrocarbon oil selected from the group consisting of synthetic oil, mineral oil, vegetable oil, animal oil, unsaturated fatty alcohol, ester of a fatty acid, $C_2$–$C_4$ mono- and polyalcohol, at least one surface-active agent possessing detergent properties selected from the group consisting of anionic, amphoteric, zwitterionic, non-ionic surface-active agents and their mixtures, said surface-active agents being present in proportions of between 5 and 50% by weight relative to the total weight of the composition, and between 0.1 and 20% by weight relative to the total weight of the composition of at least one alcohol of the formula (I):

$$R_1-X-[C_2H_3(OH)]-CH_2-Y-R_2 \qquad (I)$$

in which $R_1$ and $R_2$, which are identical or different, denote linear $C_{12}$ to $C_{20}$ alkyl groups;
X denotes an oxygen atom, a sulphur atom or a sulphoxide group;
Y denotes an oxygen or sulphur atom, a sulphoxide group or a methylene group;
the sum of the number of carbon atoms in $R_1$ and $R_2$ ranges from 24 to 40 inclusive; when X or Y denotes sulphoxide, Y or X does not denote sulphur.

2. Composition according to claim 1, wherein X denotes oxygen, Y denotes methylene and $R_1$ and $R_2$ denote radicals having 12 to 18 carbon atoms.

3. Composition according to claim 1, wherein X denotes an oxygen atom or a sulphoxide group; Y denotes an oxygen atom, a methylene or a sulphoxide group, at least one of X and Y representing a sulphoxide group.

4. Composition according to claim 1, wherein the synthetic oils have the formula:

$$H_3C-(\underset{\underset{CH_3}{|}}{\overset{\overset{CH_3}{|}}{C}}-CH_2)_n=\overset{\overset{CH_3}{|}}{CH}-CH_3 \qquad (V)$$

in which n ranges from 2 to 16.

5. Composition according to claim 1, wherein the synthetic oil is composed of a mixture of isoparaffins of formula (V):

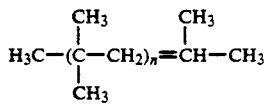

in which n ranges from 2 to 16, and of isoparaffins of the formula:

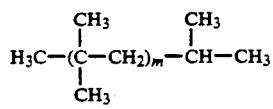

in which m is between 18 and 40.

6. Composition according to claim 4 wherein the isoparaffins of formulae (V) and (VI) are selected from the group consisting of the oils of formula (V), in which n is equal to 2, 3, 4 or 16, and in which m is equal to 38 for the isoparaffin of formula (VI).

7. Composition according to claim 1, wherein the synthetic hydrocarbon oils are fatty acid triglycerides.

8. Composition according to claim 1, wherein the mineral oil is liquid paraffin.

9. Composition according to claim 1, wherein the animal oils are selected from the group consisting of squalene, whale, seal, menhaden, halibut liver, cod liver, tuna fish, tallow, beef, caballine, mutton, vison and otter oil.

10. Composition according to claim 1, wherein the vegetable oil is selected from the group consisting of almond, peanut, wheat-germ, linseed, apricot stone, palm, pistachio, sesame, poppy seed, pine, castor, soya bean, avocado, safflower, coconut, hazelnut, olive, grape seed, sunflower, colza, cade, maize-germ, peach stone, coffee, and jojoba oils.

11. Composition according to claim 1, wherein the vegetable oil is naturally or chemically saturated.

12. Composition according to claim 1, wherein the anionic surface-active agents are selected from the group consisting of the alkali metal salts, the magnesium salts, the ammonium salts, the amine salts, the aminoalcohol salts of alkyl sulphates, alkyl ether sulphates, alkyl amidoether sulphates, alkyl aryl polyether sulphates, monoglyceride sulphates; alkyl sulphonates, alkyl amide sulphonates, alkyl aryl sulphonates, olefin sulphonates, paraffin sulphonates; alkyl sulphosuccinates, alky ether sulphosuccinates, alkyl amide sulphosuccinates; alkyl sulphosuccinamates; alkyl sulphoacetates; alkyl phosphates, alkyl ether phosphates; acyl sarcosinates, acyl isethionates, N-acyltaurates; fatty acid salts of oleic, ricinoleic, palmitic, stearic acids; copra oil, hydrogenated copra oil acids; acyl lactylates whose acyl radical contains 8 to 20 carbon atoms; and polyoxyalkylenated carboxylic ether acids; the alkyl and acyl radicals of these compounds consisting of a carbon chain containing 12 to 20 carbon atoms.

13. Composition according to claim 1, wherein the non-ionic surface-active agents are selected from the group consisting of polyethoxylated, polyoxypropylenated, polyglycerolated alcohols, alkylphenols and fatty acids, with a fatty chain containing 8 to 18 carbon atoms, the number of ethylene oxide and propylene oxide groups being between 2 and 50 and the number of glycerol groups being between 2 and 30; ethylene oxide copolymers, propylene oxide copolymers; condensates of ethylene oxides with fatty alcohols, condensates of propylene oxides with fatty alcohols; polyethoxylated fatty amides; polyglycerolated fatty amides; polyethoxylated fatty amines; oxyethylenated sorbitan fatty acid esters; sucrose glycol fatty acid esters; polyethylene glycol fatty acid esters; alkyl polyglycosides; and amine oxides.

14. Composition according to claim 1, wherein the amphoteric or zwitterionic surface-active agents are selected from the group consisting of the aliphatic secondary and tertiary amine derivatives in which the aliphatic radical is a linear or branched chain containing 8 to 18 carbon atoms and which contains at least one anionic water-solubilizing group selected from the group consisting of carboxylate, sulphonate, sulphate, phosphate, phosphonate groups; ($C_8$-$C_{20}$ alkyl)betaines, sulphotbetaines, ($C_8$-$C_{20}$ alkyl)amido($C_1$-$C_6$ alkyl)-betaines and ($C_8$-$C_{20}$ alkyl)amido($C_1$-$C_6$ alkyl)sulphobetaines.

15. Composition according to claim 1, wherein the hydrocarbon oil is used in proportions of between 0.1 and 10% by weight relative to the total weight of the composition.

16. Composition according to claim 1, wherein the alcohols containing ether and/or thioether or sulphoxide groups of formula (I) are used in proportions sufficient to ensure the suspension of the hydrocarbon oils.

17. Composition according to claim 16, wherein the alcohols containing ether and/or thioether or sulphoxide groups of formula (I) are present in proportions of between 0.5 and 10% by weight relative to the total weight of the composition.

18. Composition according to claim 1, wherein the pH is between 3 and 9.

19. Composition according to claim 1, wherein the aqueous medium is composed of water or a mixture of water and a cosmetically acceptable solvent selected from the group consisting of lower alcohols, alkylene glycols and glycol ethers, the water being present in proportions above 20%.

20. Composition according to claim 1, wherein the composition contains viscosity regulating agents selected from the group consisting of electrolytes, hydrotropic agents and thickening agents present in proportions up to 15% by weight relative to the total weight of the composition.

21. Composition according to claim 1, further containing one or more adjuvants selected from the group consisting of cationic surface-active agents, anionic, non-ionic, cationic, amphoteric polymers, optionally quaternised proteins, a silicone oil, wax, gum and resin.

22. Composition according to claim 1, further containing one or more cosmetically acceptable adjuvants selected from the group consisting of perfumes, preservatives, sequestrants, foam synergists, foam stabilisers, acidifying and alkalinising agents.

23. Method for washing and conditioning keratinous materials, comprising applying at least one composition as defined in claim 1 to these materials, and after a period of exposure, rinsing the treated materials with water.

24. In a method for suspending a hydrocarbon oil in an aqueous medium containing surface-active detergent with an agent, said surface-active detergent being selected from the group consisting of anionic, amphoteric, zwitterionic non-ionic surface-active agents and their mixtures, said surface-active agents being present in proportions of between 5 and 50% by weight relative to the total weight of the composition, the improvement wherein the agent is an alcohol of formula (I):

$$R_1-X-[C_2H_3(OH)]-CH_2-Y-R_2 \qquad (I)$$

in which
- $R_1$ and $R_2$, which are identical or different, denote linear $C_{12}$ to $C_{20}$ alkyl groups;
- X denotes an oxygen atom, a sulphur atom or a sulphoxide group;
- Y denotes an oxygen atom, a sulphur atom, a sulphoxide group or a methylene group;
- the sum of the number of carbon atoms in $R_1$ and $R_2$ ranges from 24 to 40 inclusive; when X or Y denotes sulphoxide, Y or X does not denote sulphur.

25. A method according to claim 24 wherein the sum of the number of carbon atoms in $R_1$ and $R_2$ ranges from 25 to 36 inclusive when Y denotes a methylene group and from 28 to 36 inclusive when Y does not denote a methylene group.

26. A composition according to claim 1 wherein the sum of the number of carbon atoms in $R_1$ and $R_2$ ranges from 26 to 36 inclusive when Y denotes a methylene group and from 28 to 36 inclusive when Y does not denote a methylene group.

27. Composition according to claim 1, wherein the surface-active agents are present in proportions of between 8 and 35% by weight relative to the total weight of the composition.

28. Composition according to claim 1, wherein the pH is between 3 and 8.

* * * * *